United States Patent [19]

Tóth et al.

[11] Patent Number: 4,645,774
[45] Date of Patent: Feb. 24, 1987

[54] AMINOETHOXYBENZYLALCOHOL DERIVATIVES, PROCESS FOR THEIR PREPARATION AND PHARMACEUTICAL COMPOSITIONS CONTAINING THEM

[75] Inventors: Edit Tóth; József Törley; Éva Pálosi; Szabolcs Szeberényi; László Szporny; Sándor Görög; István Hajdu, all of Budapest, Hungary

[73] Assignee: Richter Gedeon Vegyeszeti Gyar Rt, Budapest, Hungary

[21] Appl. No.: 803,792

[22] Filed: Dec. 2, 1985

Related U.S. Application Data

[63] Continuation of Ser. No. 565,834, Dec. 27, 1983, abandoned.

[30] Foreign Application Priority Data

Dec. 28, 1982 [HU] Hungary ............... 4184/82

[51] Int. Cl.$^4$ ................ A61K 31/445; C07D 295/08
[52] U.S. Cl. ....................... 514/317; 546/241; 548/575; 564/324; 564/327; 514/428; 514/648
[58] Field of Search ............... 514/317, 428; 546/241; 548/575; 564/324, 327

[56] References Cited

U.S. PATENT DOCUMENTS 4,039,589 8/1977 Toth et al. .............. 564/327 X
4,094,908 6/1978 Toth et al. .............. 564/184 X
4,551,465 11/1985 Toth et al. .............. 548/241 X Primary Examiner—Robert V. Hines
Attorney, Agent, or Firm—Karl F. Ross; Herbert Dubno

[57] ABSTRACT

The invention relates to new aminoethoxybenzylalcohol derivatives of the formula (I)

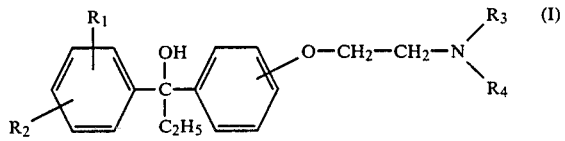

wherein $R_1$ is hydrogen, halogen, trihalomethyl, alkyl having from one to 4 carbon atoms or alkoxy having from one to 4 carbon atoms;

$R_2$ is halogen, trihalomethyl, or alkoxy having from one to 4 carbon atoms;

$R_3$ and $R_4$ stand for methyl or together with the adjacent nitrogen form an up to 8-membered ring optionally containing oxygen, and acid addition or quaternary ammonium salts thereof.

The compounds of formula (I) are pharmacologically active, thus show enzyme-inducing effect. The pharmaceutical compositions containing them as active ingredient are also within the scope of the invention.

7 Claims, No Drawings

AMINOETHOXYBENZYLALCOHOL DERIVATIVES, PROCESS FOR THEIR PREPARATION AND PHARMACEUTICAL COMPOSITIONS CONTAINING THEM

This is a continuation of co-pending application Ser. No. 565,834 filed on Dec. 27, 1983 and now abandoned.

This invention relates to new aminoethoxybenzylalcohol derivatives and salts thereof. More particularly, the invention concerns new aminoethoxybenzylalcohol derivatives of the formula (I)

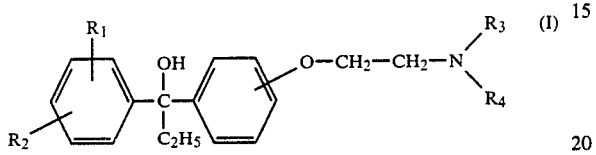

wherein
$R_1$ is hydrogen, halogen, trihalomethyl, alkyl having from one to 4 carbon atoms or alkoxy having from one to 4 carbon atoms;
$R_2$ is halogen, trihalomethyl, alkyl having from one to 4 carbon atoms or alkoxy having from one to 4 carbon atoms;
$R_3$ and $R_4$ stand for methyl or together with the adjacent nitrogen form up to an 8-membered ring optionally containing oxygen,
and acid addition or quaternary ammonium salts thereof.

The invention further relates to a process for the preparation of these compounds and pharmaceutical compositions containing them as the active ingredient.

The term "halogen" as used herein embraces all of the halogens, and may be fluorine, chlorine, bromine or iodine, preferably fluorine or chlorine.

The term "alkyl having from one to 4 carbon atoms" refers to straight or branched chained aliphatic hydrocarbon groups containing from one to 4 carbon atoms.

The term "alkoxy having from one to 4 carbon atoms" is used herein to refer to straight or branched chained alkoxy groups containing from one to 4 carbon atoms.

The trihalomethyl groups may contain any of the halogens listed above.

$R_3$ and $R_4$ together with the adjacent nitrogen preferably form a pyrrolidinyl, piperidinyl or morpholinyl ring.

Compounds of analogous structure are disclosed for example in the following references: C.A.22, 410[1]; 35, 1781[2]; 40, 4712[5]; 42,P 1015 b; 47, 9548 e; 50, 12390 c; 50, 2509 i; 55, 17915 e; 55, 15413 b; 75, P 103682 b; 76, P 11921 k; 82, 16477 g; 90, 86082 g, 92, 52927 b. None of these citations does, however, mentions any pharmaceutical activity of the disclosed compounds.

According to a further aspect of the present invention there is provided a process for the preparation of the compounds of the formula (I), wherein $R_1$, $R_2$, $R_3$ and $R_4$ have the same meaning as defined above, and salts thereof, which process comprises (a) reacting a propiophenone of the formula (II)

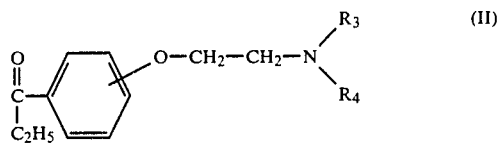

wherein $R_3$ and $R_4$ are as defined above, with an organometallic compound of the formula (III)

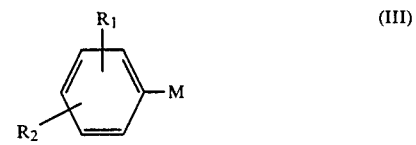

wherein
$R_1$ and $R_2$ are as defined above, and
M is an alkali metal, preferably lithium, sodium or potassium, or an MgX group, in which X is halogen; or (b) reacting a compound of the formula (IV)

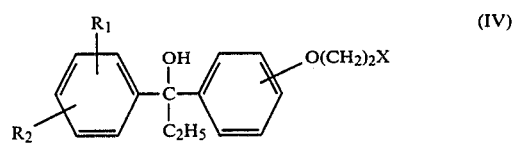

wherein
$R_1$ and $R_2$ are as defined above, and
X is halogen,
with a secondary amine of the formula (V)

wherein $R_3$ and $R_4$ are as defined above; or (c) reacting a benzophenone of the formula (VI)

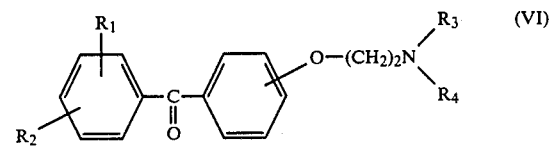

wherein $R_1$, $R_2$, $R_3$ and $R_4$ are as defined above, with an organometallic compound containing an ethyl group, preferably an ethyl magnesium halide or ethyl lithium; or (d) reacting a propiophenone of the formula (VII)

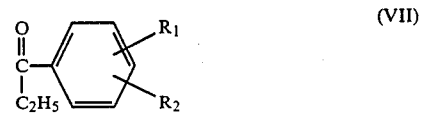

wherein $R_1$ and $R_2$ are as defined above, with a Grignard compound of the formula (VIII)

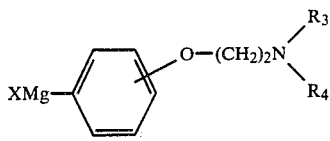

(VIII)

wherein
R$_3$ and R$_4$ are as defined above, and
X is halogen; or
(e) reacting a compound of the formula (IX)

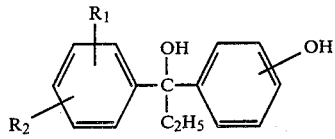

(IX)

wherein R$_1$ and R$_2$ are as defined above, preferably in the form of an alkali metal or quaternary ammonium phenolate thereof, with a tertiary amine of the formula (X)

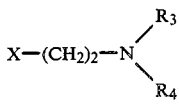

(X)

wherein
R$_3$ and R$_4$ are as defined above, and
X is an alkyl sulfonyloxy or aryl sulfonyloxy group or halogen,
preferably in the presence of an acid binding agent,
and if desired, converting any of the products obtained by process variants (a) to (e) into their acid addition or quaternary ammonium salts, or converting a product obtained as an acid addition salt into a corresponding base and/or converting a free base into an acid addition or quaternary ammonium salt thereof.

The starting compounds are known or can be prepared by methods known in the art.

The ketones of the formulae (II), (VI) and (VII) can for example be synthesized by the Friedel-Crafts type ketone synthesis (G. A. Olah: Friedel-Crafts and Related Reactions, III/1, Ed.: Interscience Publishers 1964, pp. 1-63).

The compounds of the formulae (III) and (VIII) are for example prepared by preparing Grignard reactants from the corresponding aryl halides by known techniques (M. S. Kharash et al.: Grignard Reactions of Nonmetallic Substances, Ed., Prentice-Hall. Inc. (1954) pp. 5-90), while the alkali metal-organic compounds can be prepared following the method disclosed in Houben-Weyl: Methoden der Organischen Chemie, XIII/1, pp. 134-159 and 389-405 (1970).

The compounds of the formulae (IV) and (IX) can for example be synthesized from the corresponding substituted propiophenones by reaction with the corresponding Grignard reactants (see e.g. M. S. Kharash et al.: Grignard Reactions of Non-metallic Substances, Ed.: Prentice-Hall Inc. (1954) pp. 134-143).

According to a preferred embodiment of process variant a) propiophenones of the formula (II) are reacted with the organometallic compounds of the formula (III), preferably appropriately substituted phenyl magnesium chloride or bromide or phenyl lithium, in a dry inert organic solvent. The reaction is preferably carried out in an aprotic organic solvent, e.g. in an aliphatic ether such as diethyl ether, di-n-butyl ether or diethylene glycol dimethyl ether, an alicyclic ether such as tetrahydrofurane, dioxane, an aliphatic or aromatic hydrocarbon such as ligroin, benzene, toluene, xylene, dimethyl sulfoxide or hexamethyl phosphorus amide, or a mixture of these solvents. The organometallic compound is used in an at least equimolar amount. The reaction is preferably performed in an inert gas atmosphere, e.g. nitrogen or argon. The reaction temperature may range from −60° C. up to the boiling point of the solvent, and preferably is between −30° C. and 100° C. When the reaction is complete, the reaction mixture is decomposed, preferably with an aqueous ammonium chloride solution, and the obtained compound of the formula (I) is separated. The product can be purified by known techniques, e.g. by distillation or crystallization.

According to process variant (b) a compound of the formula (IV), in which X preferably represents chlorine or bromine, is reacted with a secondary amine of the formula (V). The reaction is preferably performed in an organic solvent, in the presence of a base suitable for binding the acid formed in the reaction. As a solvent for example hydrocarbons such as ligroin, benzene, toluene, halogenated hydrocarbons such as chloroform, ethers such as dioxane, alcohols such as ethanol, esters such as ethyl acetate, acid amides such as dimethyl formamide, ketones such as acetone, methyl isobutyl ketone, or a mixture of these solvents are employed. Suitable acid binding agents include for example inorganic or tertiary organic bases, but an excess amount of the amine of the formula (V) may also be used. If the excess of an amine of the formula (V) or a tertiary organic base is used to bind the hydrogen halide formed in the reaction, these may as well serve as a solvent. The reaction can be carried out at a temperature between 20° C. and the boiling temperature of the solvent employed. When the reaction is complete, the product is isolated. The reaction mixture may then be poured onto water, and the product may be eliminated e.g. by solvent extraction. The organic phase is then washed halogen-free with water, dried and evaporated. The crude product can be purified by distillation or crystallization.

According to process variant (c) a benzophenone of the formula (VI) is reacted with an at least equimolar amount of an ethyl-containing organometallic compound, preferably ethyl magnesium bromide or ethyl magnesium iodide or ethyl lithium. The reaction is carried out in an inert dry organic solvent, as described in connection with process variant (a).

According to process variant (d) Grignard compounds of the formula (VIII), preferably containing bromine in place of X, are reacted with an at least equimolar amount of the propiophenones of the formula (VII), in a dry inert organic solvent, similarly to process variant (a).

According to a preferred embodiment of process variant (e) compounds of the formula (IX) are condensed with the tertiary amines of the formula (X) preferably in the form of their alkali metal or quaternary ammonium phenolates. As a tertiary amine for example a tosylate, mesylate, bromide or preferably chloride of a compound of the formula (X) is employed, as a free base or a salt, e.g. hydrogen halide thereof. The reaction is preferably carried out in an inert solvent, in the presence of an acid binding agent, under anhydrous conditions or in a mixture of water and an organic solvent. As organic solvents for example esters such as ethyl acetate, ethers such as dioxane, tetrahydrofuran or diethyl ether, hydrocarbons such as ligroin, benzene, toluene or xylene, halogenated hydrocarbons such as chloroform, chlorobenzene, acid amides such as dimethyl formamide, ketones such as acetone, methyl ethyl ketone or methyl isobutyl ketone, alcohols such as ethanol, propanol, etc. are employed. Compounds of the formula (IX) can be converted into their phenolates by methods known in the art, e.g. using alkali metal alcoholates, amides, hydrides, hydroxides, carbonates or quaternary ammonium compounds. Preferred acid binding agents include inorganic and tertiary organic bases, e.g. sodium hydroxide, potassium hydroxide, potassium carbonate, triethyl amine, pyridine, etc. The reaction is optionally performed in the presence of a catalyst. As a catalyst for example alkali metal halides, preferably alkali metal iodides may be used. The reaction temperature may be varied within a wide range, and preferably is between 20° C. and the boiling point of the reaction mixture.

If desired, the compounds of the formula (I) can be converted into their acid addition salts or quaternary ammonium salts by methods known in the art. The acid addition salts can be prepared by means of inorganic and organic acids, e.g. hydrogen halides such as hydrochloric acid, hydrogen bromide, etc., sulfuric acid, phosphoric acids, formic acid, acetic acid, propionic acid, oxalic acid, glycolic acid, maleic acid, fumaric acid, tartaric acid, succinic acid, ascorbic acid, citric acid, malic acid, salicylic acid, lactic acid, benzoic acid, cinnamic acid, asparaginic acid, glutaminic acid, N-acetyl-asparaginic acid, N-acetyl-glutaminic acid, alkylsulfonic acids such as methanesulfonic acid, arylsulfonic acids such as p-toluene-sulfonic acid, etc.

According to a preferred embodiment the corresponding acid is added to a solution of a compound of the formula (I) in an inert solvent, e.g. ethanol, and the salt formed is precipitated, preferably with a water-immiscible organic solvent such as diethyl ether. Quaternization is preferably carried out with a lower alkyl, alkenyl or benzyl halide or alkyl sulfate. The reaction is performed in an organic solvent, preferably acetone, acetonitrile, ethanol or in a mixture of these solvents, at a temperature between room temperature and the boiling point of the solvent. The quaternary salts can be isolated for example by filtration and if desired, are purified by crystallization.

The compounds of the formula (I) provided by the invention are pharmacologically active. In particular, they induce the polysubstrate mono-oxygenase enzyme system of the liver, which plays an essential role in the regulation of metabolic processes, in the biotransformation of endogenic and exogenic substances. This enables their widespread use in therapy, for example in enzymopathic icterus, Gilbert disease, neonatal hyperbilirubenaemias, Cushing disease, Stein-Leventhal and Crigler-Najjar syndroms, thyrotoxic crises, intrahepatic cholestases, nutritive allergies (increase of the efficiency of diagnostic methods, e.g. cholecistography). As an enzyme inducing compound generally phenobarbital is used in therapy, it has, however CNS (sedative, despiration-depressing) side-effect when administered in the effective dose. Therefore, there is a great demand for selective enzyme inducing compounds, which are devoid of undesired pharmacodynamic side-effects.

The enzyme-inducing potency of the new compounds according to the invention was determined by several methods. One of these methods was the in vivo measurement of hexobarbital oxidase activity.

To determine the change of hexobarbital oxidase activity female Hann.-Wistar rats, each weighing 50 to 60 g. were treated orally with a single 40 mg./kg. dose of the active agent. One and 24 hours after the administration of the active agent, respectively, the animals were narcotized with a 60 mg./kg. i.v. dose of hexobarbital sodium, and the time elapsed until complete wakening from ceasing of the righting reflex was measured (Noordhoex J.: Eur. J. Pharmacol, 3, 242, 1968). As a reference compound phenobarbital was used. The data were recorded, and the mean values, the standard errors, as well as the percentage increase with respect to the control were calculated for each group. The results are shown in Table 1. Abbreviations:
$\bar{x}$ = mean value,
S.E. = standard error of the mean value,
n = number of animals.

The control group was treated with a placebo.

$$\text{Control} = 37.8 \pm 3.9 \; \bar{x} \pm S.E. \; \text{min.} \quad (1)$$

$$35.2 \pm 1.78 \; \bar{x} \pm S.E. \; \text{min.} \quad (2)$$

A = α-ethyl-α-(3-trifluoromethylphenyl)-4-[2-(piperidin-1-yl)-ethoxy]-benzylalcohol;
B = α-ethyl-α-(3-trifluoromethylphenyl)-4-[2-(dimethylamino)-ethoxy]-benzylalcohol;
C = α-ethyl-α-(2-methoxyphenyl)-4-[2-(pyrrolidin-1-yl)-ethoxy]-benzylalcohol;
D = α-ethyl-α-(4-fluorophenyl)-4-[2-(piperidin-1-yl)-ethoxy]-benzylalcohol.

TABLE 1

| Compound (40 mg./kg.) | Narcosis period in % of the control | | n |
|---|---|---|---|
| | 1 hour | 24 hours | |
| A | 177 ± 5.0 | 49 ± 0.7 | 10 |
| B | 180 ± 10.0 | 49 ± 3.3 | 10 |
| C | 113 ± 12.0 | 57 ± 7.8 | 10 |
| D | 120 ± 4.2 | 53 ± 3.7 | 10 |
| phenobarbital | 250 ± 15.8 | 60 ± 7.3 | 10 |
| control | 100 ± 10.3 (1) | 100 ± 5.0 (2) | 10 |

The decrease of narcosis period is due to the fact that the new compounds according to the invention accelerate the conversion of hexobarbital, a foreign substance in the body, into an inactive metabolite. As appears from the data of Table 1, the new compounds according to the invention are equal or superior to phenobarbital with respect to their effect shown in the above test. Their important advantage in comparison with phenobarbital is that they have no inhibition phase or at least their inhibition phase is considerably smaller than that of phenobarbital.

The enzyme inducing activity of the compounds of the formula (I) was further tested by determining the activity of the polysubstrate monooxygenase enzyme system of the liver after treatment with a placebo and the compounds according to the invention, respectively. Female H. Wistar rats each weighing 50 to 60 g. were administered a single 40 mg./kg. dose of the test compounds, orally. 24 hours after treatment the animals were decapitated and the livers were eliminated. After rinsing with a physiological saline solution at 0° C., drying and weighing, the livers were homogenized in a 0.1 molar Tris-HCl buffer (pH=7.4) containing 1.15% of potassium chloride at 0° C., centrifuged at 900 g for 20 minutes, and the supernatant (postmitochondrial fraction) was used for further investigations. The microsomal fraction was prepared following the method developed by Cinti D. L. et al.: Biochem. Pharmacol., 21, 3249 (1972). The cytochrome P-450 concentration was determined from the carbon monoxide differential spectrum of a reduced microsomal suspension (Omura T. et al.: J. Biol. Chem. 239, 2370 (1964)), the quantity of cytochrome b-5 was determined from a NADH differential spectrum (Raw J. et al.: J. Biol. Chem. 234, 1867 (1959)). The activity of NADPH: ferricytochrome C (P-450) reductase (E.C. 1.6.2.4) was measured according to Williams C. H. et al.: J. Biol. Chem. 237, 587 (1962). The activity of aniline hydroxylase was determined according to Chhabra R. S. et al.: Toxicol. Appl. Pharmacol., 22, 50 (1972) by measuring the velocity of p-aminophenol formation, while the aminopyridine demethylase activity was determined on the basis of the quantity of formaldehyde formed, following the method of Gourlay G. K. et al.: Biochem. Pharmacol., 27, 965 (1978).

The results shown in Table 2 are expressed in % of the control. the control groups were treated with a placebo.

TABLE 2

|  | Control $\bar{x} \pm$ S.E. 100% $\pm$ S.E. % | Compound D |
|---|---|---|
| Relative weight of liver | 4.3 ± 0.17 | 122 ± 4.9% |
| g./100 g. of body weight | 100 ± 3.9% | |
| Microsomal protein | 29.3 ± 1.01 | 111 ± 4.2% |
| mg./g. of liver | 100 ± 3.4% | |
| Cytochrome b-5 | 8.6 ± 0.43 | 116 ± 4.8% |
| nmoles/g. of liver | 100 ± 5.0% | |
| Cytochrome P-450 | 12.8 ± 0.63 | 163 ± 8.7% |
| nmoles/g. of liver | 100 ± 4.9% | |
| c(P-450)reductase | 4686 ± 286.2 | 178 ± 16.2% |
| nmoles/g. of liver/min. | 100 ± 6.1% | |
| Aniline hydroxylase | 20.3 ± 0.88 | 131 ± 5.9% |
| nmoles/g. of liver/min. | 100 ± 4.3% | |
| Aminopyridine demethylase | 254.8 ± 7.47 | 123 ± 7.8% |
| nmoles/g./min. | 100 ± 2.9% | |

From the data presented in Table 2 it appears that the new compounds according to the invention considerably increase the quantity/activity of the components of microsomal electron transport chain, i.e. induce the enzyme system responsible for the biotransformation of xenobiotics.

The acute toxicity of the compounds of the formula (I) was determined on H-Wistar rats of both sexes, each weighing 160 to 180 g. The compounds were administered in a single 500 mg./kg. dose, orally. The animals were observed for 14 days. The results, expressed in % of the perished animals, are set forth in Table 3.

TABLE 3

| Compound (500 mg./kg. p.o.) | Perished animals | n |
|---|---|---|
| A | ∅ | 10 |
| B | ∅ | 10 |
| C | ∅ | 10 |
| D | ∅ | 10 |
| Phenobarbital[x] | 100 | 10 |

[x]$LD_{50}$ = 245 mg./kg.
∅ = 0%

As appears from the data of Table 3, the toxicity of the instant compounds is much lower than that of phenobarbital, accordingly their therapeutic index is much more favorable.

The central nervous activities of the compounds according to the invention were examined on mice and rats with the following methods: electroshock (Swinyard, E. A., Brown, W. C., Goodman, L. S.: J. Pharmacol. Exp. Ther. 106, 319 (1952)), metrazole spasm (Everett, G. M., Richards, R. K.: J. Pharmacol. Exp. Ther. 81, 402 (1944)), thiosemicarbazide spasm (Da Venzo, J. P., Greig, M. E., Cormin, M. A.: Amer. J. Physiol. 201, 833 (1961)), strychnine spasm (Kerley, T. L., Richards, A. G., Begley, R. W., Abreu, B. B., Wesver, L. C.: J. Pharmacol. Exp. Ther. 132, 360 (1961)), nicotine spasm (Stone, C. A., Mecklenburg, K. L., Torhans, M. L.: Arch. Int. Pharmacodyn. 117, 419 (1958)), rotarod test (Kinnard, W. C., Carr, C. J.: J. Pharmacol. Expt. Ther. 121, 354 (1957)), physostigmine lethality preventing effect (Nose, T., Kojima, M.: Europ. J. Pharmacol. 10, 83 (1970)), yohimbine potentiation effect (Quinton, R. M.: Brit. J. Pharmacol. 21, 51 (1963)), and analgesic activity (Bianchi, G., Francheschini, J.: Brit. J. Pharm. Chemother. 9, 280 (1954)).

As a reference substance, phenobarbital was used. Both the compounds under examination and the reference substance were administered orally, in dosages of 40 and 80 mg./kg., respectively. The compounds according to the invention were completely ineffective, whereas phenobarbital exerted strong anticonvulsive muscle-coordinating and sedative effects even in a dose of 40 mg./kg. Consequently, the new compounds according to the invention have the further advantage over phenobarbital that they are devoid of central nervous activities.

The pharmacologically active compounds according to the invention can be used in therapy in the form of pharmaceutical compositions, which are formulated as preparations suitable for oral, rectal and/or parenteral administration. For oral administration tablets, dragees or capsules are prepared. The oral formulations contain as a vehicle e.g. lactose or starch, as an excipient or a granulation aid e.g. gelatine, carboxymethyl cellulose, polyvinyl pyrrolidone or starch gum, as a disintegrating substance e.g. potato starch or microcrystalline cellulose, ultraamlyopectine or formaldehyde casein, etc. The formulations may also contain antiadhesives and lubricants such as talc, colloidal silica, stearin, calcium or magnesium stearate, etc.

Tablets are prepared for example by wet granulation and subsequent pressing. A mixture of the active ingredient and the vehicle and optionally a portion of the disintegrating agent are granulated with an aqueous, alcoholic or aqueous-alcoholic solution of the excipients in suitable equipment, and the granules are dried. The remaining portions of the disintegrating substance, lubricant, antiadhesive or optional further additives are then added to the granules, and the mixture is pressed to tablets. If desired, the tablets are prepared with a dividing line, which facilitates administration. Tablets can be prepared also from a mixture of the active ingredient and suitable additives by direct pressing.

If desired, the tablets can be converted into dragees, using protecting, flavoring agents and pigments generally known for the preparation of pharmaceutical compositions, e.g. sugar, cellulose derivatives (methyl or ethyl cellulose, carboxymethyl cellulose sodium, etc.), polyvinylpyrrolidone, calcium phosphate, calcium carbonate, food pigments, food oil varnishes, aroma substances, iron oxide pigments, etc.

Capsules are prepared by filling a mixture of the active ingredient and the additives into suitable capsules.

For rectal administration the compositions are formulated as suppositories, which contain in addition to the active ingredient a carrier mass, called adeps pro suppository. Suitable carriers include vegetable fats, e.g. hardened vegetable oils, triglycerides of fatty acids having 12 to 18 carbon atoms, preferably Witepsol (a registered trade mark). The active ingredient is homogeneously distributed in the melted carrier mass, and suppositories are prepared by casting.

For parenteral administration injectable preparations are prepared. To prepare an injectable solution the active ingredient is dissolved in distilled water and/or various organic solvents, e.g. glycol ethers, optionally in the presence of dissolution aids, e.g. polyoxyethylene sorbitan monolaurate, monooleate or monostearate (Tween 20, Tween 60, Tween 80). The injectable solutions may contain also various additives, e.g. preserving agents such as benzyl alcohol, p-oxy-benzoic acid methyl or propyl ester, benzalkonium chloride or phenyl mercuri borate, etc., antioxidants such as ascorbic acid, tocopherol, sodium pyrosulfate and optionally complexing agents to bind the metal traces such as ethylene diamine tetraacetate, buffers to adjust the pH and optionally local anaesthetics such as lidocaine. The injectable solutions are filtered, filled into ampoules and sterilized. The daily dose, depending on the state of the patient, varies between 1.0 and 200.0 mg./kg., preferably 5.0 and 50 mg./kg., preferably administered in smaller portions.

The invention will be further described with reference to the following illustrative Examples.

EXAMPLE 1

α-Ethyl-α-(3-trifluoromethylphenyl)-4-[2-(dimethylamino)-ethoxy]-benzylalcohol

To a Grignard reactant prepared from 1.82 g. of magnesium turnings and 16.9 g. of 3-bromobenzotrifluoride in 60 ml. of tetrahydrofurane a solution of 11.1 g. of 4-[2-(dimethylamino)-ethyl]-propiophenone in 26 ml. of tetrahydrofurane is added dropwise, with stirring under slight reflux. The reaction mixture is slightly boiled for two additional hours, whereupon it is cooled and poured onto a 25% aqueous ammonium chloride solution. The phases are separated, and the aqueous phase is extracted with tetrahydrofurane. The solvent phases are combined, washed to neutral with a saturated ammonium chloride solution, dried over anhydrous magnesium sulfate, and tetrahydrofurane is distilled off under reduced pressure. The residue is crystallized from n-heptane. 11.9 g. of the title compound are obtained, melting at 109 to 110 ° C.

Analysis for $C_{20}H_{24}F_3NO_2$: Calculated: C 65.38%, H 6.58%, F 15.51%, N 3.81%; Found: C 65.47%, H 6.55%, F 15.68%, N 3.9%.

Upon treating the dry ethereal solution of the base with hydrochloric acid in ether, under cooling, the hydrochloride salt precipitates in a crystalline form, which is then filtered off and dried. Melting point: 108° to 109° C.

To a solution of the base in dry ethanol an ethanolic solution of fumaric acid is added. After dilution with dry ether the crystalline fumarate is filtered off, and dried. Melting point: 128° to 129° C.

EXAMPLE 2

α-Ethyl-α-(3-trifluoromethylphenyl)-4-[2-(dimethylamino)-ethoxy]-benzylalcohol methoiodide 3.7 g. of α-ethyl-α-(3-trifluoromethylphenyl)-4-[2-(dimethylamino)-ethoxy]-benzylalcohol are dissolved in 20 ml. of acetone, 1 ml. of methyl iodide are added, and the reaction mixture is slightly boiled for one hour. After cooling, the crystalline quaternary ammonium salt is filtered off, and dried to yield 4.3 g. of the named compound, melting at 69° to 70° C.

Similarly there can be prepared the following compounds by proper selection of the starting substances:
α-ethyl-α-(2-methoxyphenyl)-4-[2-(pyrrolidin-1-yl)-ethoxy]-benzylalcohol methoiodide, melting point: 96° to 97° C.;
α-ethyl-α-(4-fluorophenyl)-4-[2-(piperidin-1-yl)-ethoxy]-benzylalcohol ethoiodide, melting point: 94° to 95° C.

EXAMPLE 3

α-Ethyl-α-(4-fluorophenyl)-4-[2-(piperidin-1-yl)-ethoxy]-benzylalcohol 17.6 g. of α-ethyl-α-(4-fluorophenyl)-4-(2-bromoethoxy)-benzylalcohol and 30 ml. of dry piperidine are refluxed with stirring for two hours. Piperidine is distilled off from the reaction mixture under reduced pressure, to the residue water is added, and it is extracted with ether. The ethereal phase is washed to neutral with water, dried over anhydrous potassium carbonate, and then ether is distilled off. Crystallization of the residue from n-hexane yields 14.9 g. of the named compound, melting at 72° to 73° C.

Analysis for $C_{22}H_{28}FNO_2$: Calculated: C 73.92%, H 7.90%, F 5.31%, N 3.92%; Found: C 74.07%, H 7.86%, F 5.50%, N 3.88%.

Melting point of hydrochloride: 180° to 181° C.
Melting point of hydrofumarate: 159° to 160° C.
Melting point of hydrogen citrate: 77° to 78° C.

EXAMPLE 4

α-Ethyl-α-(2-methoxyphenyl)-4-[2-(pyrrolidin-1-yl)-ethoxy]-benzylalcohol 6.5 g. of α-ethyl-α-(2-methoxyphenyl)-4-hydroxybenzylalcohol, 0.4 g. of tetrabutylammonium hydrogensulfate, 7 g. of anhydrous potassium carbonate and 3.7 g. of 2-(pyrrolidin-1-yl)-ethyl chloride in 80 ml. of ethyl acetate are refluxed for 16 hours. After cooling the solvent is distilled off in vacuo, and to the residue water and ether are added. The phases are separated, and the aqueous phase is extracted with ether. The combined ethereal phases are washed to neutral with a 5% aqueous potassium hydroxide solution and subsequently with water, dried over anhydrous magnesium sulfate, filtered, and evaporated to dryness. Crystallization of the residue from ethyl acetate yields 6.9 g. of the named compound, melting at 113° to 114° C.

Analysis for $C_{22}H_{29}NO_3$: Calculated: C 74.33%, H 8.22%, N 3.94%; Found: C 74.46%, H 8.37%, N 4.11%.

Melting point of hydrochloride: 136° to 137° C.
Melting point of hydrogen fumarate: 134° to 135° C.

EXAMPLE 5

α-Ethyl-α-(3-chlorophenyl)-4-[2-(dimethylamino)-ethoxy]-benzylalcohol

To a Grignard reactant prepared from 2.2 g. of magnesium turnings and 23.4 g. of 4-[2-(dimethylamino)-ethoxy]-bromobenzene in 100 ml. of dry tetrahydrofurane a solution of 10 g. of m-chloro-propiophenone in 30 ml. of tetrahydrofurane is added dropwise, at 20° C. The reaction mixture is stirred at room temperature for another two hours, cooled, and filtered onto a 20% aqueous ammonium chloride solution. Tetrahydrofurane is distilled off in vacuo. The residue is extracted with ether, the ethereal phase is washed with water, dried over anhydrous magnesium sulfate, filtered, and ether is distilled off. Crystallization of the residue from a mixture of n-hexane and ethyl acetate yields 14.2 g. of the named compound, melting at 108° to 109° C.

Analysis for $C_{19}H_{21}ClNO_2$: Calculated: C 68.35%, H 7.25%, Cl 10.62%, N 4.20%; Found: C 68.33%, H 7.40%, Cl 10.78%, N 4.27%.

EXAMPLE 6

α-Ethyl-α-(3-trifluoromethylphenyl)-4-[2-(morpholin-4-yl)-ethoxy]-benzylalcohol

To a Grignard reactant prepared from 2.4 g. of magnesium turnings and 11 g. of ethyl bromide in 40 ml. of dry ether a solution of 9.5 g. of 3-trifluoromethyl-4'-[2-(morpholin-1-yl)-ethoxy]-benzophenone in 100 ml. of dry ether is added dropwise, at 0° C. The reaction mixture is stirred for 30 additional minutes at 0° C., and is then refluxed for one hour. After cooling, the reaction mixture is poured onto a 10% aqueous ammonium chloride solution. The ethereal phase is separated, the aqueous phase is extracted with ether. The ethereal solution is washed to neutral with water, dried over anhydrous magnesium sulfate, filtered, and ether is distilled off under reduced pressure. Crystallization of the residue from n-hexane yields 5.2 g. of the named compound, melting at 73° to 74° C.

Analysis for $C_{22}H_{26}F_3NO_3$:
Calculated: C 64.53%, H 6.40%, F 13.92%, N 3.42%; Found: C 64.66%, H 6.51%, F 14.10%, N 3.44%.

EXAMPLE 7

α-Ethyl-α-(4-fluorophenyl)-4-[2-(dimethylamino)-ethoxy]-benzylalcohol

To an ethyl lithium solution prepared from 10.9 g. of ethyl bromide and 1.4 g. of lithium metal in 120 ml. of dry ether, in argon atmosphere a solution of 14.3 g. of 4-fluoro-4'-[2-(dimethylamino)-ethoxy]-benzophenone in 210 ml. of dry ether is added dropwise at −30° C., whereupon the reaction mixture is stirred for en additional hour. The mixture is then decomposed with a 10% aqueous ammonium chloride solution. The aqueous phase is extracted with ether, the ethereal phase is washed to neutral with water, dried over anhydrous magnesium sulfate, and ether is distilled off under reduced pressure. Crystallization of the solid residue from a mixture of ethyl acetate and n-hexane yields 13.4 g. of the named compound, melting at 85° to 86° C.

Analysis for $C_{19}H_{24}FNO_2$: Calculated: C 71.89%, H 7.62%, F 5.99%, N 4.41%; Found: C 72.03%, H 7.64%, F 6.20%, N 4.47%.

EXAMPLE 8

α-Ethyl-α-(3-trifluoromethylphenyl)-4-[2-(piperidin-1-yl)-ethoxy]-benzylalcohol 8.9 g. of α-ethyl-α-(3-trifluoromethylphenyl)-4-hydroxy-benzylalcohol, 13.7 g. of anhydrous potassium carbonate and 6.1 g. of N-(2-chloroethyl)-piperidine hydrochloride are slightly boiled in 90 ml. of methyl isobutyl ketone for three hours, under reflux. The solvent is distilled off in vacuo, to the residue water is added, and it is extracted with benzene. The benzene phase is washed to neutral with a 5% aqueous potassium hydroxide solution and subsequently with water, and dried over anhydrous magnesium sulfate. The solvent is distilled off under reduced pressure, and the residue is crystallized from n-hexane to yield 9.8 g. of the named compound, melting at 100° to 101° C.

Analysis for $C_{23}H_{28}F_3NO_2$: Calculated: C 67.79%, H 6.93%, F 14.00%, N 3.44%;
Found: C 67.90%, H 6.89%, F 13.97%, N 3.53%.
Melting point of hydrochloride: 154° to 155° C.
Melting point of hydrogen fumarate: 99° C.

Similarly there can be prepared the following compounds by proper selection of the starting substances:

α-ethyl-α-(3-chlorophenyl)-4-[2-(piperidin-1-yl)-ethoxy]-benzylalcohol, melting point: 109° to 110° C.
Analysis for $C_{22}H_{28}ClNO_2$:
Calculated: C 70.66%, H 7.55%, Cl 9.48%, N 3.75%; Found C 70.68%, H 7.38%, Cl 9.60%, N 3.67%.

α-ethyl-α-(2-methoxyphenyl)-4-[2-(dimethylamino)-ethoxy]-benzylalcohol, melting point: 80° to 81° C.
Analysis for $C_{20}H_{27}NO_3$:
Calculated: C 72.92%, H 8.26%, N 4.25%; Found: C 73.10%, H 8.33%, N 4.17%.

α-ethyl-α-(2,5-dimethylphenyl)-4-[2-(dimethylamino)-ethoxy]-benzylalcohol, melting point: 105° to 106° C.
Analysis for $C_{21}H_{29}NO_2$: Calculated: C 77.02%, H 8.93%, N 4.28%; Found: C 77.07%, H 9.10%, N 4.35%.

α-ethyl-α-(2-methoxyphenyl)-4-[2-(piperidin-1-yl)-ethoxy]-benzylalcohol, melting point: 72° to 73° C.
Analysis for $C_{23}H_{31}NO_3$: Calculated: C 74.76%, H 8.46%, N 3.79%; Found: C 74.70%, H 8.55%, N 3.92%.

α-ethyl-α-(4-chlorophenyl)-4-[2-(dimethylamino)-ethoxy]-benzylalcohol, melting point: 73° to 74° C.
Analysis for $C_{19}H_{21}ClNO_2$: Calculated: C 68.35%, H 7.25%, Cl 10.62%, N 4.20%; Found: C 68.57%, H 7.33%, Cl 10.66%, N 4.38%.

EXAMPLE 9

Preparation of pharmaceutical compositions

| Tablets | |
|---|---|
| Composition of a single tablet: | |
| α-ethyl-α-(2-methoxyphenyl)-4-[2-(pyrrolidin-yl)-ethoxy]-benzylalcohol | 50.0 mg. |
| lactose | 92.0 mg. |
| potato starch | 40.0 mg. |
| polyvinyl pyrrolidone | 4.0 mg. |
| talc | 6.0 mg. |
| magnesium stearate | 1.0 mg. |
| ultraamylopectine | 6.0 mg. |
| aerosil (colloidal $SiO_2$) | 1.0 mg. |
| | 200.0 mg. |

The active ingredient is admixed with the lactose, potato starch and polyvinyl pyrrolidone, wetted with ethanol and granulated. The granules are dried at a temperature not exceeding 40° C., passed through a sieve, admixed with the remaining additives and pressed into tablets.

| Suppositories | |
|---|---|
| Composition of a suppository: | |
| α-ethyl-α-(4-fluorophenyl)-4-[2-(piperidin-1-yl)-ethoxy]-benzylalcohol | 100.0 mg. |
| lactose | 200.0 mg. |
| basic substance (e.g. Witepsol H) | 1700.0 mg. |
| | 2000.0 mg. |

The active ingredient is thoroughly admixed with the lactose. The basic substance is melted, cooled to 35° C. and admixed with a mixture of the active ingredient and lactose in a homogenizer. The obtained mass is filled into cool molds.

| Capsules | |
|---|---|
| Composition of a single capsule: | |
| α-ethyl-α-(3-trifluoromethylphenyl)-4-[2-(piperidin-1-yl)-ethoxy]-benzylalcohol | 50.0 mg. |
| lactose | 130.0 mg. |
| potato starch | 37.0 mg. |
| talc | 2.0 mg |
| aerosil (colloidal SiO$_2$) | 1.0 mg. |
| microcrystalline cellulose | 5.0 mg. |
| | 225.0 mg. |

Capsule size: 2

The active ingredient is admixed with the lactose and potato starch, ground, and the further ingredients are added. the mixture is homogenized, passed through a 0.32-mm. sieve, and filled into hard gelatine capsules.

We claim:

1. A compound of the Formula (I)

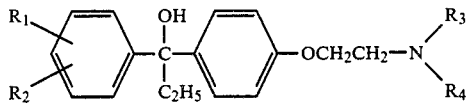

wherein
$R_1$ is hydrogen;
$R_2$ is halo, trihalomethyl, or $C_1$ to $C_4$ alkoxy; and
$R_3$ and $R_4$ together with the adjacent nitrogen atom form a piperidinyl, or pyrrolidinyl, group; or a pharmaceutically acceptable acid addition or quaternary ammonium salt thereof.

2. The compound of the Formula (I) defined in claim 1 selected from the group consisting of:
   (a) alpha-ethyl-alpha-(2-methoxy-phenyl)-4-[2-pyrrolidin-1-yl)-ethoxy]-benzyl alcohol;
   (b) alpha-ethyl-alpha-(4-fluorophenyl)-4-[2-piperidin-1-yl-ethoxy]-benzyl alcohol;
   (c) alpha-ethyl-alpha-(3-trifluoromethyl-phenyl)-4-[2-(piperidin-1-yl)-ethoxy]-benzyl alcohol;
   (d) alpha-ethyl-alpha-(3-chloro-phenyl)-4-[2-piperidin-1-yl)-ethoxy]-benzyl alcohol; and
   (e) alpha-ethyl-alpha-(2-methoxyphenyl)-4-[2-piperidin-1-yl)-ethoxy]-benzyl alcohol; or a pharmaceutically acceptable acid addition or quaternary ammonium salt thereof.

3. Alpha-ethyl-alpha-(3-trifluoromethyl-phenyl)-4-[2-(piperidin-1-yl)-ethoxy]-benzyl alcohol as defined in claim 1 or a pharmaceutically acceptable acid addition or quaternary ammonium salt thereof.

4. Alpha-ethyl-alpha-(2-methoxyphenyl)-4-[2-pyrrolidin-1-yl)-ethoxy]-benzyl alcohol as defined in claim 1 or a pharmaceutically acceptable acid addition or quaternary ammonium salt thereof.

5. Alpha-ethyl-alpha-(4-fluorophenyl)-4-[2-(piperidin-1-yl)-ethoxy]-benzyl alcohol as defined in claim 1 or a pharmaceutically acceptable acid addition or quaternary ammonium salt thereof.

6. A pharmaceutical composition for inducing the polysubstrate liver monooxygenase enzyme system containing a pharmaceutically effective amount of the compound of the Formula (I) as defined in claim 1 or a pharmaceutically acceptable acid addition or quaternary ammonium salt thereof, together with a pharmaceutically acceptable carrier or auxiliary substance.

7. A method of inducing the polysubstrate liver monooxygenase enzyme system in a susceptible subject which comprises administering to said subject an effective amount of the compound of the Formula (I) defined in claim 1 or a pharmaceutically acceptable acid addition or quaternary ammonium salt thereof.

* * * * *